US012729117B2

(12) United States Patent
Mukawa et al.

(10) Patent No.: US 12,729,117 B2
(45) Date of Patent: Sep. 8, 2026

(54) SPRAY AGENT PACKED IN CONTAINER AND METHOD FOR PRODUCING THE SAME

(71) Applicants: Nippon Ekitan Corporation, Tokyo (JP); Taiko Pharmaceutical Co., Ltd., Osaka (JP)

(72) Inventors: Rei Mukawa, Tokyo (JP); Hideaki Nochide, Tokyo (JP); Chiharu Tomita, Tokyo (JP); Kenkichi Aoki, Suita (JP); Kazuhiko Taguchi, Suita (JP); Shohei Tsujimoto, Suita (JP)

(73) Assignees: Nippon Ekitan Corporation, Tokyo (JP); Taiko Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 18/843,053

(22) PCT Filed: Mar. 2, 2023

(86) PCT No.: PCT/JP2023/007728
§ 371 (c)(1),
(2) Date: Aug. 30, 2024

(87) PCT Pub. No.: WO2023/167270
PCT Pub. Date: Sep. 7, 2023

(65) Prior Publication Data

US 2025/0171302 A1 May 29, 2025

(30) Foreign Application Priority Data

Mar. 3, 2022 (JP) ................................ 2022-032843

(51) Int. Cl.

| | |
|---|---|
| ***C01B 11/02*** | (2006.01) |
| ***F17C 5/02*** | (2006.01) |
| *A61L 2/20* | (2006.01) |

(52) U.S. Cl.
CPC .............. *C01B 11/022* (2013.01); *F17C 5/02* (2013.01); *A61L 2/20* (2013.01); *C01B 11/02* (2013.01); *F17C 2221/03* (2013.01)

(58) Field of Classification Search
CPC .......... C01B 11/022; C01B 11/02; F17C 5/02; F17C 2221/03; F17C 2221/013; A61L 2/20; A61L 12/102; A01N 25/06
(Continued)

(56) References Cited

U.S. PATENT DOCUMENTS 3,084,995 A * 4/1963 Grubitsch ............. C01B 11/022 252/372
4,456,511 A * 6/1984 Fisher .................... B01J 19/122 204/157.48

(Continued)

FOREIGN PATENT DOCUMENTS

CN 113003540 A * 6/2021 ........... C01B 11/024
EP 0519152 A1 12/1992

(Continued)

OTHER PUBLICATIONS

JP-2002143278-A English Translation of Specification (Year: 2025).*

(Continued)

*Primary Examiner* — Craig M Schneider
*Assistant Examiner* — Stephanie A Shrieves
(74) *Attorney, Agent, or Firm* — McDonnell Boehnen Hulbert & Berghoff LLP

(57) ABSTRACT

A spray agent packed in a container includes chlorine dioxide ($ClO_2$) and liquefied carbon dioxide gas ($LCO_2$) charged in a pressure-resistant container B, wherein the chlorine dioxide ($ClO_2$) is dissolved in the liquefied carbon dioxide gas ($LCO_2$) within the pressure-resistant container B.

2 Claims, 4 Drawing Sheets

(58) Field of Classification Search
USPC ..... 141/4; 252/187.21, 372; 422/28, 40, 477
See application file for complete search history.

(56) References Cited

U.S. PATENT DOCUMENTS

| | | | | |
|---|---|---|---|---|
| 4,855,135 | A | 8/1989 | Ratcliff | |
| 5,707,546 | A * | 1/1998 | Pitochelli | C01B 11/022<br>206/524.4 |
| 7,077,297 | B1 | 7/2006 | Valentini | |
| 7,799,198 | B2 * | 9/2010 | Nanjundiah | C02F 1/4674<br>204/233 |
| 9,295,262 | B2 * | 3/2016 | Kato | A01N 59/08 |
| 2016/0068393 | A1 * | 3/2016 | Doona | C01B 11/024<br>423/477 |
| 2019/0292436 | A1 * | 9/2019 | Mason | E21B 43/164 |

FOREIGN PATENT DOCUMENTS

| | | | | |
|---|---|---|---|---|
| JP | 06-009202 | A | 1/1994 | |
| JP | 2002143278 | A * | 5/2002 | |
| KR | 101977036 | B1 * | 5/2019 | C01B 11/024 |
| KR | 102217544 | B1 * | 2/2021 | C02F 1/50 |
| TW | 200302113 | A | 8/2003 | |
| TW | 201916895 | A | 5/2019 | |

OTHER PUBLICATIONS

CN-113003540-A English Translation of Specification (Year: 2025).*
KR-101977036-B1 English Translation of Specification (Year: 2025).*
KR-102217544-B1 English Translation of Specification (Year: 2025).*
International Search Report for corresponding PCT application No. PCT/JP2023/007728 dated May 9, 2023.
Taiwan Patent Office, Taiwan Office Action and Search Report for corresponding Taiwan application No. 112107482 dated Mar. 16, 2026.

* cited by examiner 1
2
3
4
5
6
7
8
9
10
11a
11b
12a
12b
13a
13b
14a
14b
15
16
17
18
19
20
21
21a
22
23
24
25
100
B
G
L
α
β
α, β
$ClO_2$, $GCO_2$
$GCO_2$
$LCO_2$ 1
6
100
B
24
29
$LCO_2$
28
14b
5
21
22
9
G
10
L
β
11b
12b
β
13b
23
21a
7
2
20
8
3
11a
α
12a
α
13a
15
$ClO_2$, $GCO_2$
$GCO_2$
α, β
18
17
14a
15
$GCO_2$
4
16
19

1
100
25
$LCO_2$
B
6
14b
β
11b
12b
β
13b
23
22
9
G
10
L
21
5
30
24
3
21a
7
2
20
8
11a
12a
α
13a
14a
α
15
18
17
$ClO_2$, $GCO_2$
$GCO_2$
α, β
15
$GCO_2$
4
16
19

SPRAY AGENT PACKED IN CONTAINER AND METHOD FOR PRODUCING THE SAME

CROSS-REFERENCE TO RELATED APPLICATIONS

The present application is a U.S. National Phase Application pursuant to 35 U.S.C. § 371 of PCT International Application No. PCT/JP2023/007728 filed Mar. 2, 2023, which claims priority to Japanese Patent Application No. 2022-032843, filed Mar. 3, 2022, the contents of each of which are incorporated herein by reference.

TECHNICAL FIELD

The present invention relates to a spray agent packed in a container and a method for producing the same.

BACKGROUND ART

For example, chlorine dioxide ($ClO_2$) has long been known to have a bleaching effect, and many methods have been used to produce it. However, industrially produced high-concentration chlorine dioxide is a strong oxidizing agent, may react with other substances to produce high-concentration chlorine, and may pose a slight risk of explosion.

Therefore, chlorine dioxide which is less dangerous and easier to handle is used in the form of a 5% aqueous solution of chlorine dioxide that is appropriately diluted in accordance with the application. Chlorine dioxide gas vaporized from such an aqueous chlorine dioxide solution is safe as it does not have a strong and irritating odor, and when it comes into contact with an object, it exerts various effects such as being highly bactericidal, antiviral, deodorizing, and disinfecting.

Although chlorine dioxide exerts such excellent effects, it is usually transported in the form of an aqueous solution, and therefore care must be taken when it is handled.

In order to address such problems, a method and device for supplying a sterilizing mixed gas in which a stabilized chlorine dioxide aqueous solution is mixed with carbon dioxide in a liquid or vapor state, and a mixed gas of a predetermined concentration is released into a target space through a pressure and/or temperature adjustable mixing means have been proposed (refer to Patent Document 1).

CITATION LIST

Patent Document

Patent Document 1

Japanese Unexamined Patent Application, First Publication No. 2002-143278

SUMMARY OF INVENTION

Technical Problem

However, in the invention described in the above-described Patent Document 1, not only is it difficult to store the aqueous chlorine dioxide solution for a long period of time, but a container may be corroded by the aqueous chlorine dioxide solution. Furthermore, in the invention described in Patent Document 1, when chlorine dioxide is sprayed into a space for use, this may be considered as a production of high-pressure gas under the High Pressure Gas Safety Act, making it difficult to implement in accordance with the High Pressure Gas Safety Act.

The present invention has been proposed in view of the above-described conventional circumstances, and an object thereof is to provide a spray agent packed in a container which has excellent preservation properties for chlorine dioxide and is suitable for spraying chlorine dioxide into a space, and a method for producing the same.

Solution to Problem

In order to achieve the aforementioned objects, the present invention provides the following means:

[1] A spray agent packed in a container including chlorine dioxide and liquefied carbon dioxide gas charged into a pressure-resistant container, wherein the chlorine dioxide is dissolved in the liquefied carbon dioxide gas within the pressure-resistant container.

[2] The spray agent packed in a container described in [1], in which a concentration of the chlorine dioxide in the liquefied carbon dioxide gas is $1\times10^{-2}$ to $1\times10^{5}$ ppm.

[3] A method for producing a spray agent packed in a container, including generating chlorine dioxide, charging a pressure-resistant container with the chlorine dioxide, and dissolving the chlorine dioxide in liquefied carbon dioxide gas while the pressure-resistant container charged with the chlorine dioxide is charged with the liquefied carbon dioxide gas.

[4] The method for producing a spray agent packed in a container described in [3], in which while the chlorine dioxide is generated by reacting a chemical liquid in a reaction tank, a carrier gas is flowed into the chemical liquid in the reaction tank to perform bubbling, and the chlorine dioxide generated in the reaction tank is charged into the pressure-resistant container together with the carrier gas.

[5] The method for producing a spray agent packed in a container described in [4], in which carbon dioxide gas is used as the carrier gas.

[6] The method for producing a spray agent packed in a container described in [3], in which the chlorine dioxide generated by reacting the chemical liquid is charged into the pressure-resistant container.

Advantageous Effects of Invention

As described above, according to the present invention, it is possible to provide a spray agent packed in a container that has excellent preservation properties for chlorine dioxide and is suitable for spraying chlorine dioxide into a space, and a method for producing the same.

DESCRIPTION OF EMBODIMENTS

Figure 1:
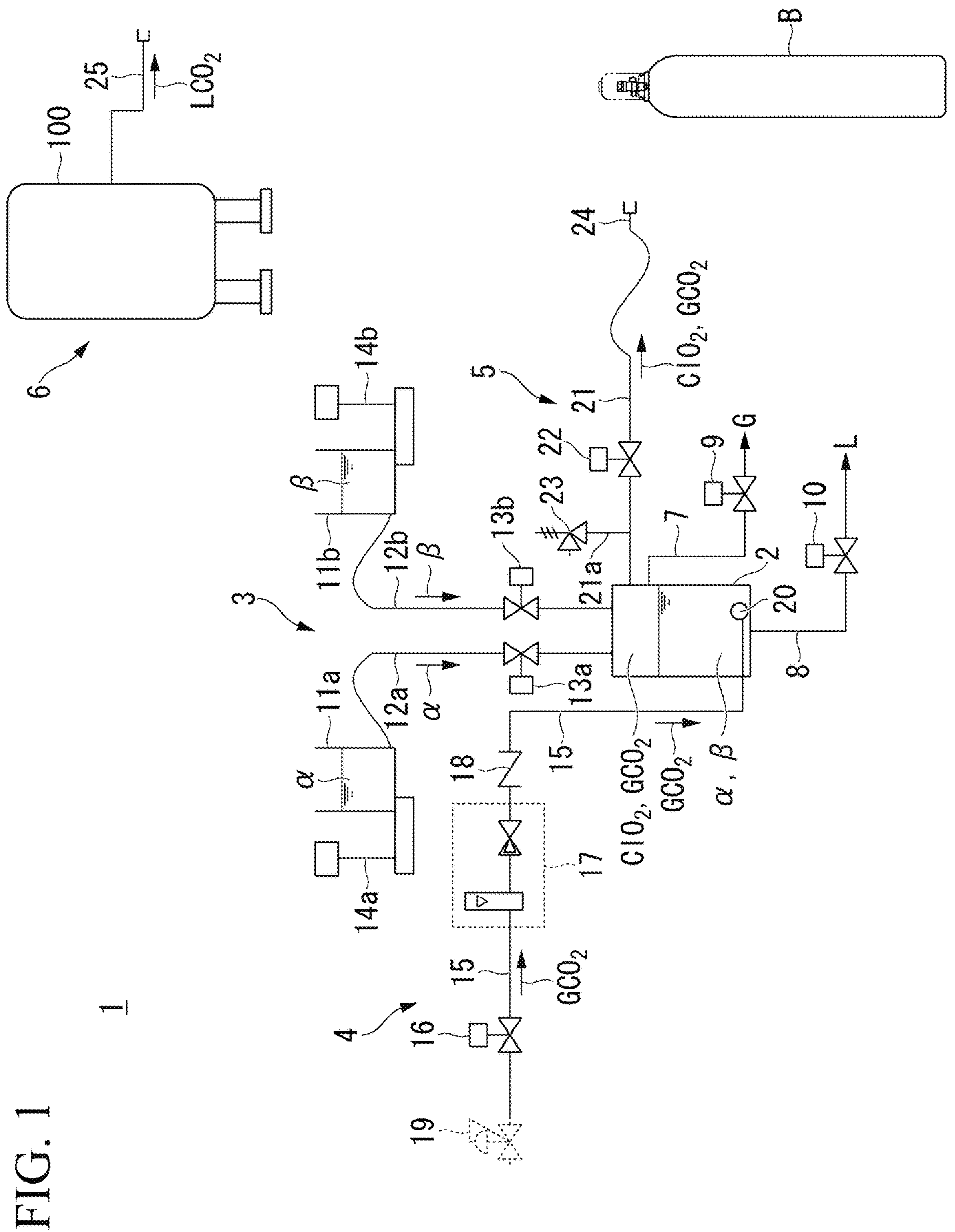
FIG. 1 is a schematic diagram showing a configuration of a system for producing a spray agent packed in a container according to one embodiment of the present invention.

Hereinafter, an embodiment of the present invention will be described in detail with reference to the drawings.

Spray Agent Packed in Container

First, a spray agent packed in a container to which the present invention is applied will be described.

The spray agent packed in a container to which the present invention is applied contains chlorine dioxide ($ClO_2$) and liquefied carbon dioxide gas ($LCO_2$) charged in a pressure-resistant container, and the chlorine dioxide is dissolved in the liquefied carbon dioxide gas within the pressure-resistant container.

In addition, in the spray agent packed in a container to which the present invention is applied, a concentration of the chlorine dioxide in the liquefied carbon dioxide gas is preferably $1\times10^{-2}$ to $1\times10^{5}$ ppm, more preferably $1\times10^{-1}$ to $1\times10^{4}$ ppm, and further preferably $1\times10^{-1}$ to $5\times10^{3}$ ppm.

As for the pressure-resistant container, a siphon-type gas cylinder in which liquefied carbon dioxide gas with chlorine dioxide dissolved therein is extracted in a liquid phase state is preferably used. As for the pressure-resistant container, a general gas cylinder in which liquefied carbon dioxide gas with chlorine dioxide dissolved therein is extracted in a gas phase state may be used. In this case, when a general gas cylinder is used in an upside-down state, it is possible to extract the liquefied carbon dioxide gas with chlorine dioxide dissolved therein in a liquid phase state.

As for the spray agent packed in a container to which the present invention is applied, in addition to extracting the liquefied carbon dioxide gas with chlorine dioxide dissolved therein in a liquid phase from the pressure-resistant container described above, it is also possible to extract it in a gas phase from the pressure-resistant container, that is, as a mixed gas of chlorine dioxide and carbon dioxide gas.

In the spray agent packed in a container to which the present invention is applied, liquefied carbon dioxide gas with chlorine dioxide dissolved therein is sprayed into a space to be cleaned from a tip end (a spray outlet) of a spray nozzle connected to the pressure-resistant container. Thus, it is possible to clean the space with chlorine dioxide in carbon dioxide gas ($GCO_2$) vaporized within the space.

Therefore, by using the spray agent packed in a container to which the present invention is applied, it is possible to achieve a variety of effects such as being highly bactericidal, antiviral, deodorizing, and disinfecting. In addition, by spraying this spray agent packed in a container onto the object to be cleaned, it is possible to exert various effects such as high bactericidal, antiviral, deodorizing, and disinfecting effects on an object to be cleaned.

In the spray agent packed in a container to which the present invention is applied, chlorine dioxide is present in a state in which it is dissolved in liquefied carbon dioxide gas within the above-described pressure-resistant container. In this case, the chlorine dioxide is not decomposed, and the chlorine dioxide can be stored in a stable state within the pressure-resistant container.

In addition, in the spray agent packed in a container to which the present invention is applied, chlorine dioxide is present in a state in which it is dissolved in liquefied carbon dioxide gas within the above-described pressure-resistant container, and thus it is possible to prevent corrosion of the pressure-resistant container by the chlorine dioxide.

Method for Producing Spray Agent Packed in Container

Next, a method for producing a spray agent packed in a container to which the present invention is applied will be described.

The method for producing a spray agent packed in a container to which the present invention is applied includes a step of generating chlorine dioxide, a step of charging a pressure-resistant container with the chlorine dioxide, and a step of dissolving the chlorine dioxide in liquefied carbon dioxide gas while charging the liquefied carbon dioxide gas into the pressure-resistant container charged with the chlorine dioxide.

In addition, in the method for producing a spray agent packed in a container to which the present invention is applied, preferably, bubbling is performed by flowing a carrier gas into a chemical liquid in a reaction tank, and chlorine dioxide generated in the reaction tank is charged into the pressure-resistant container together with the carrier gas. On the other hand, it is also possible to charge the pressure-resistant container with chlorine dioxide generated by reacting the chemical liquid without using the carrier gas.

As for the carrier gas, carbon dioxide gas ($GCO_2$), which does not react with chlorine dioxide, can be suitably used. On the other hand, as for the carrier gas, in addition to the above-described carbon dioxide gas, it is also possible to use, for example, nitrogen ($N_2$) gas, inert gases such as argon (Ar) and helium (He), dry air (synthetic air), or the like.

Examples of methods for generating chlorine dioxide include a method of using a mixture of a chlorite and an acid material, a method of using a mixture of a chlorite, a hypochlorite and an acid material, and a method of using a mixture of a chlorite and chlorine gas. In addition, the methods for generating chlorine dioxide include a method of electrolyzing a chlorite aqueous solution and a method using a catalyst, and are not necessarily limited to a method of mixing chemical liquids.

Examples of the chlorites include alkali metal chlorites and alkaline earth metal chlorites. Examples of the alkali metal chlorites include sodium chlorite, potassium chlorite, and lithium chlorite. Examples of the alkaline earth metal chlorites include calcium chlorite, magnesium chlorite, and barium chlorite. Among them, from the viewpoint of ease of availability, it is preferable to use sodium chlorite or potassium chlorite, and it is more preferable to use sodium chlorite. These chlorites may be used alone or in combination of two or more.

Examples of the hypochlorites include alkali metal hypochlorites and alkaline earth metal hypochlorites. Examples of the alkali metal hypochlorites include sodium hypochlorite, potassium hypochlorite, and lithium hypochlorite. Examples of the alkaline earth metal hypochlorites include calcium hypochlorite, magnesium hypochlorite, and barium hypochlorite. Among them, from the viewpoint of ease of availability, it is preferable to use sodium hypochlorite and potassium hypochlorite, and it is more preferable to use sodium hypochlorite. These hypochlorites may be used alone or in combination of two or more.

Examples of the acid materials include inorganic acids such as hydrochloric acid, sulfuric acid, sulfurous acid, thiosulfuric acid, nitric acid, carbonic acid, nitrous acid, iodic acid, phosphoric acid, phosphorous acid, sodium hydrogen sulfate, potassium hydrogen sulfate, and chromic acid, and organic acids such as formic acid, acetic acid, propionic acid, butyric acid, lactic acid, pyruvic acid, citric acid, malic acid, tartaric acid, gluconic acid, glycolic acid, fumaric acid, malonic acid, maleic acid, oxalic acid, succinic acid, acrylic acid, crotonic acid, and glutaric acid, but the present invention is not necessarily limited to these acid materials. Moreover, these acid materials may be used alone or in combination of two or more.

System for Producing Spray Agent Packed in Container

Next, as one embodiment of the present invention, a production system 1 of a spray agent packed in a container, for example as shown in FIG. 1, will be described.

FIG. 1 is a schematic diagram showing a configuration of the system 1 for producing a spray agent packed in a container.

The production system of this embodiment produces the above-described spray agent packed in a container to which the present invention is applied.

Specifically, as shown in FIG. 1, the production system 1 includes a reaction tank 2 that generates chlorine dioxide ($ClO_2$) by mixing and reacting chemical liquids α and β, a chemical liquid supply unit 3 that supplies the chemical liquids α and β to the reaction tank 2, a carrier gas supply unit 4 that supplies carbon dioxide gas ($GCO_2$) as a carrier gas to the reaction tank 2, a chlorine dioxide charging unit 5 that charges the chlorine dioxide ($ClO_2$) generated in the reaction tank 2 into a pressure-resistant container B, and a liquefied carbon dioxide gas charging unit 6 that charges liquefied carbon dioxide gas ($LCO_2$) as a spray gas into the pressure-resistant container charged with the chlorine dioxide ($ClO_2$).

As shown in FIG. 1, the reaction tank 2 is, for example, a substantially cylindrical sealed container that has chemical resistance and pressure resistance so as not to react with the chemical liquids α and β and chlorine dioxide ($ClO_2$). The reaction tank 2 is connected to a waste gas pipe 7 for discharging waste gas G generated in the reaction tank 2, and a waste liquid pipe 8 for discharging waste liquid L generated in the reaction tank 2.

The waste gas pipe 7 is connected to the upper side of the reaction tank 2 so as not to come into contact with the chemical liquids α and β and the waste liquid L. In addition, a first on-off valve 9 for opening and closing the waste gas pipe 7 is provided in the waste gas pipe 7.

The waste liquid pipe 8 is connected to the bottom side of the reaction tank 2 so as to be able to discharge the waste liquid L. In addition, a second on-off valve 10 for opening and closing the waste liquid pipe 8 is provided in the waste liquid pipe 8.

The chemical liquid supply unit 3 includes a first chemical liquid tank 11*a* for accommodating the chemical liquid α, a second chemical liquid tank 11*b* for accommodating the chemical liquid β, a first chemical liquid supply pipe 12*a* for supplying the chemical liquid α from the first chemical liquid tank 11*a* to the reaction tank 2, a second chemical liquid supply pipe 12*b* for supplying the chemical liquid β from the second chemical liquid tank 11*b* to the reaction tank 2, a third on-off valve 13*a* for opening and closing the first chemical liquid supply pipe 12*a*, and a fourth on-off valve 13*b* for opening and closing the second chemical liquid supply pipe 12*b*.

The chemical liquids α and β are liquids containing a substance for generating the above-described chlorine dioxide ($ClO_2$). The first chemical liquid tank 11*a* and the second chemical liquid tank 11*b* are disposed on load cells 14*a* and 14*b*, respectively. Thus, amounts of supply of the chemical liquids α and β can be measured by the load cells 14*a* and 14*b*.

The first chemical liquid tank 11*a* and the second chemical liquid tank 11*b* are disposed above the reaction tank 2. One end of each of the first chemical liquid supply pipe 12*a* and the second chemical liquid supply pipe 12*b* is connected to the bottom side of each of the first chemical liquid tank 11*a* and the second chemical liquid tank 11*b*, and the other end thereof is connected to the top side of the reaction tank 2.

Thus, the chemical liquids α and β accommodated in the first chemical liquid tank 11*a* and the second chemical liquid tank 11*b* can be supplied to the reaction tank 2 via the first chemical liquid supply pipe 12*a* and the second chemical liquid supply pipe 12*b* by their own weight.

The chemical liquids α and β can be supplied to the reaction tank 2 by a supply means such as a pump without being limited to the above-described method for supplying them by their own weight.

The carrier gas supply unit 4 includes a carrier gas supply pipe 15 for supplying the carrier gas ($GCO_2$) to the reaction tank 2, a fifth on-off valve 16 for opening and closing the carrier gas supply pipe 15, a mass flow controller (MFC) 17 that adjusts a flow rate of the carrier gas ($GCO_2$) flowing through the carrier gas supply pipe 15, and a check valve 18 that prevents backflow from the reaction tank 2 side.

One end of the carrier gas supply pipe 15 is connected to the reaction tank 2, and the other end thereof is connected via a pressure reducing valve 19 to a tank or cylinder (not shown) in which liquefied carbon dioxide gas is stored. The carrier gas is supplied as gas-phase carbon dioxide gas ($GCO_2$) from the tank or cylinder.

One end of the carrier gas supply pipe 15 is located at the lower side inside the reaction tank 2, and a bubbler 20 is mounted on a tip end thereof. Thus, bubbling is performed by flowing the carrier gas ($GCO_2$) through the bubbler 20 into the chemical liquids α and β in the reaction tank.

The reaction of the chemical liquids α and β in the reaction tank 2 is promoted by such bubbling. In addition, chlorine dioxide ($ClO_2$) generated in the reaction tank 2 is stored above the chemical liquids α and β in the reaction tank 2 together with the carrier gas ($GCO_2$).

The means for promoting the reaction of the chemical liquids α and β in the reaction tank 2 is not necessarily limited to the configuration using the bubbler 20 described above, and any means capable of bubbling may be used. It is also possible to provide a means for stirring the chemical liquids α and β in the reaction tank 2 and a means for heating the chemical liquids α and β in the reaction tank 2.

The fifth on-off valve 16 is disposed between the MFC 17 of the carrier gas supply pipe 15 and the pressure reducing valve 19. The MFC 17 is disposed between the fifth on-off valve 16 of the carrier gas supply pipe 15 and the check valve 18. The check valve 18 is disposed between the MFC 17 of the carrier gas supply pipe 15 and the reaction tank 2. The fifth on-off valve 16 may be disposed between the MFC 17 of the carrier gas supply pipe 15 and the reaction tank 2.

The chlorine dioxide charging unit 5 includes a chlorine dioxide discharge pipe 21 for discharging the chlorine dioxide ($ClO_2$) generated in the reaction tank 2 together with the carrier gas ($GCO_2$), a sixth on-off valve 22 for opening and closing the chlorine dioxide discharge pipe 21, and a pressure relief valve 23 that opens when the pressure in the reaction tank 2 reaches a set value (for example, 0.1 MPa) or higher.

One end of the chlorine dioxide discharge pipe 21 is connected to the reaction tank 2, and the other end thereof is connected to a connection hose 24. The sixth on-off valve 22 is disposed in the chlorine dioxide discharge pipe 21 between the reaction tank 2 and the connection hose 24. The pressure relief valve 23 is disposed in a pipe 21*a* that branches off from the chlorine dioxide discharge pipe 21 between the reaction tank 2 and the sixth on-off valve 22.

Thus, the connection hose 24 is connected to the pressure-resistant container B, so that the chlorine dioxide ($ClO_2$) generated in the reaction tank 2 can be charged into the pressure-resistant container B together with the carrier gas ($GCO_2$).

The liquefied carbon dioxide gas charging unit 6 has a connection hose 25 connected to a tank or cylinder 100 in which liquefied carbon dioxide gas ($LCO_2$) is stored. In the liquefied carbon dioxide gas charging unit 6, the connection hose 25 is connected to the pressure-resistant container B, and while the pressure-resistant container B is charged with the liquefied carbon dioxide gas, chlorine dioxide ($ClO_2$) is dissolved in the liquefied carbon dioxide gas ($LCO_2$).

Producing Process of Spray Agent Packed in Container

Next, a producing process of a spray agent packed in a container using the production system 1 will be described.

In the production system 1 of this embodiment, first, as shown in FIG. 1, the first to sixth on-off valves 9, 10, 13*a*, 13*b*, 16, and 22 are closed, and then the first and fifth on-off valves 9 and 16 are opened. In addition, the flow rate of the carrier gas ($GCO_2$) flowing through the carrier gas supply pipe 15 is set to an arbitrary value by the MFC 17.

Thus, the carrier gas ($GCO_2$) is supplied to the reaction tank 2 via the carrier gas supply pipe 15, and unnecessary waste gas G in the reaction tank 2 is discharged to the outside of the reaction tank 2.

Next, after the reaction tank 2 is charged with the carrier gas, the third on-off valve 13*a* is opened, a fixed amount of the chemical liquid α is added to the reaction tank 2, and then the third on-off valve 13*a* is closed. In addition, the fourth on-off valve 13*b* is opened, a fixed amount of the chemical liquid β is added to the reaction tank 2, and then the fourth on-off valve 13*b* is closed.

Thus, the chemical liquids α and β react in the reaction tank 2 to generate chlorine dioxide ($ClO_2$). In addition, the carrier gas ($GCO_2$) is caused to flow through the chemical liquids α and β in the reaction tank 2 to perform bubbling.

Next, the reaction of the chemical liquids α and β in the reaction tank 2 proceeds, the chlorine dioxide ($ClO_2$) generated in the reaction tank 2 is stored together with the carrier gas ($GCO_2$) above the chemical liquids α and β in the reaction tank 2, and then a flow rate of the carrier gas ($GCO_2$) flowing through the carrier gas supply pipe 15 is set to 0 L/min by the MFC 17. Then, the first on-off valve 9 is closed, and the sixth on-off valve 22 is opened.

The pressure-resistant container B that has been evacuated in advance is connected to the connection hose 24. Thus, due to a pressure difference between the reaction tank 2 and the pressure-resistant container B, the chlorine dioxide ($ClO_2$) stored in the reaction tank 2 is charged into the pressure-resistant container B together with the carrier gas ($GCO_2$). After the charging has started, the pressure-resistant container B is charged with the carrier gas ($GCO_2$) at a flow rate of an arbitrary value by the MFC 17.

Next, after a degree of vacuum in the pressure-resistant container B becomes 0 MPa, the fifth and sixth on-off valves 16 and 22 are closed. Then, the first on-off valve 9 is opened, and the unnecessary waste gas G in the reaction tank 2 is discharged to the outside of the reaction tank 2. In addition, the second on-off valve 10 is opened to discharge unnecessary waste liquid L from the reaction tank 2 to the outside of the reaction tank 2.

Next, the connection hose 25 is connected to the pressure-resistant container B charged with chlorine dioxide ($ClO_2$), and liquefied carbon dioxide gas ($LCO_2$) is charged into the pressure-resistant container B while being pressurized. Thus, the liquefied carbon dioxide gas ($LCO_2$) is charged into the pressure-resistant container B so that the concentration of the chlorine dioxide ($ClO_2$) in the liquefied carbon dioxide gas ($LCO_2$) becomes a predetermined concentration while the chlorine dioxide ($ClO_2$) is dissolved in the liquefied carbon dioxide gas ($LCO_2$) in the pressure-resistant container B.

The above-described carrier gas remains in the pressure-resistant container B, but this does not have any particular effect on the spray agent packed in a container, and the carrier gas may remain in the pressure-resistant container B.

By going through the above processes, it is possible to produce a spray agent packed in a container to which the present invention is applied.

The present invention is not necessarily limited to the above-described embodiment, and various modifications can be made without departing from the spirit of the present invention.

Figure 2:
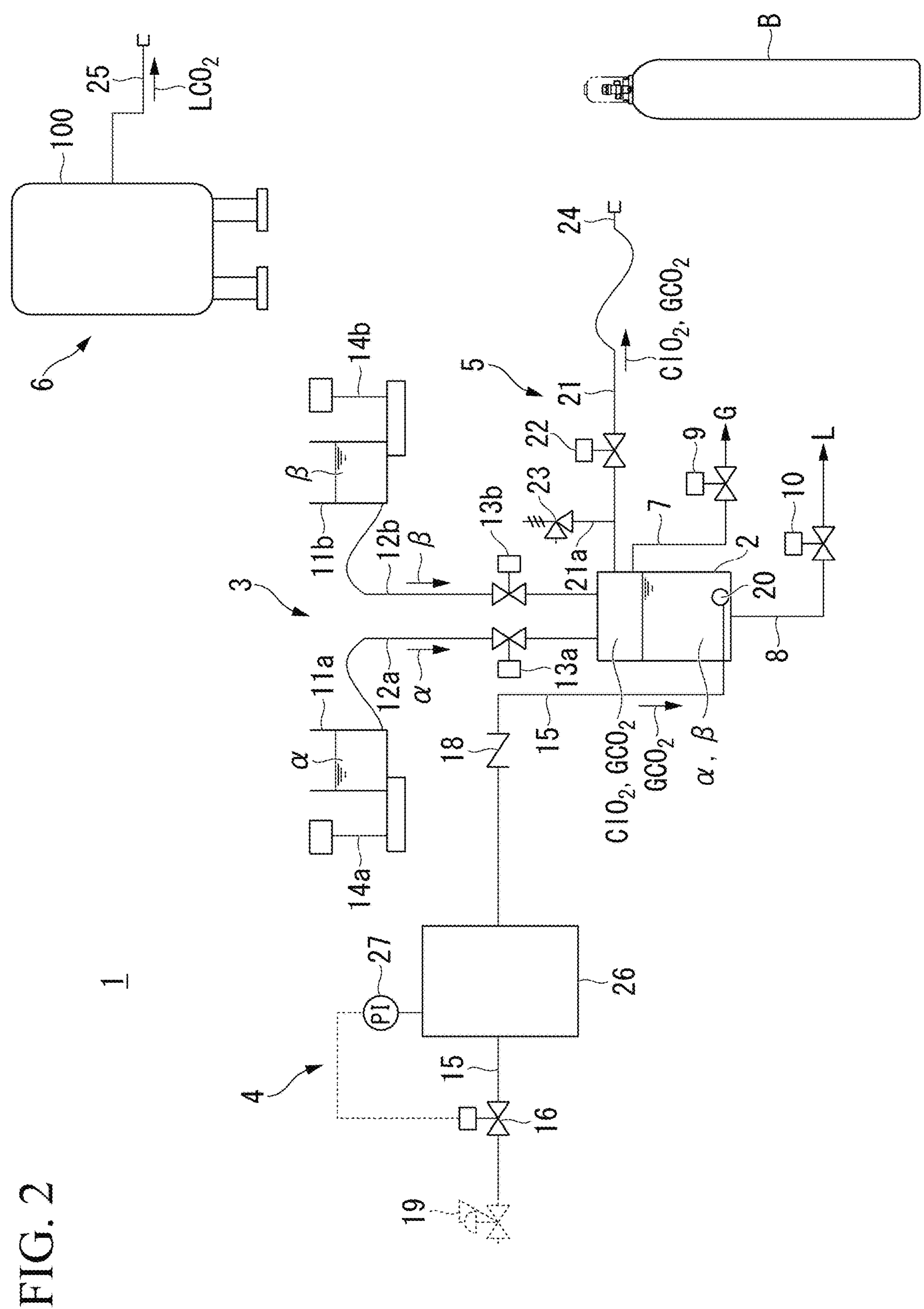
FIG. 2 is a schematic diagram showing a modified example of the system for producing a spray agent packed in a container shown in FIG. 1.

For example, the production system 1 may be configured to include a buffer tank 26 and a pressure sensor 27 as shown in FIG. 2, instead of the MFC 17.

The buffer tank 26 temporarily stores the carrier gas ($GCO_2$) flowing through the carrier gas supply pipe 15, and is disposed between the fifth on-off valve 16 and the check valve 18 of the carrier gas supply pipe 15.

The pressure sensor 27 is connected to the buffer tank 26 and measures a pressure inside the buffer tank 26. The pressure sensor 27 is also connected to the fifth on-off valve 16 and is capable of controlling the opening and closing of the fifth on-off valve 16.

In the configuration shown in FIG. 2, the carrier gas ($GCO_2$) supplied to the reaction tank 2 can be adjusted by the pressure.

The production system 1 is not necessarily limited to the above-described configuration, and for example, it is also possible to add a buffer tank 26 and a pressure sensor 27 to the configuration shown in FIG. 1.

Figure 3:
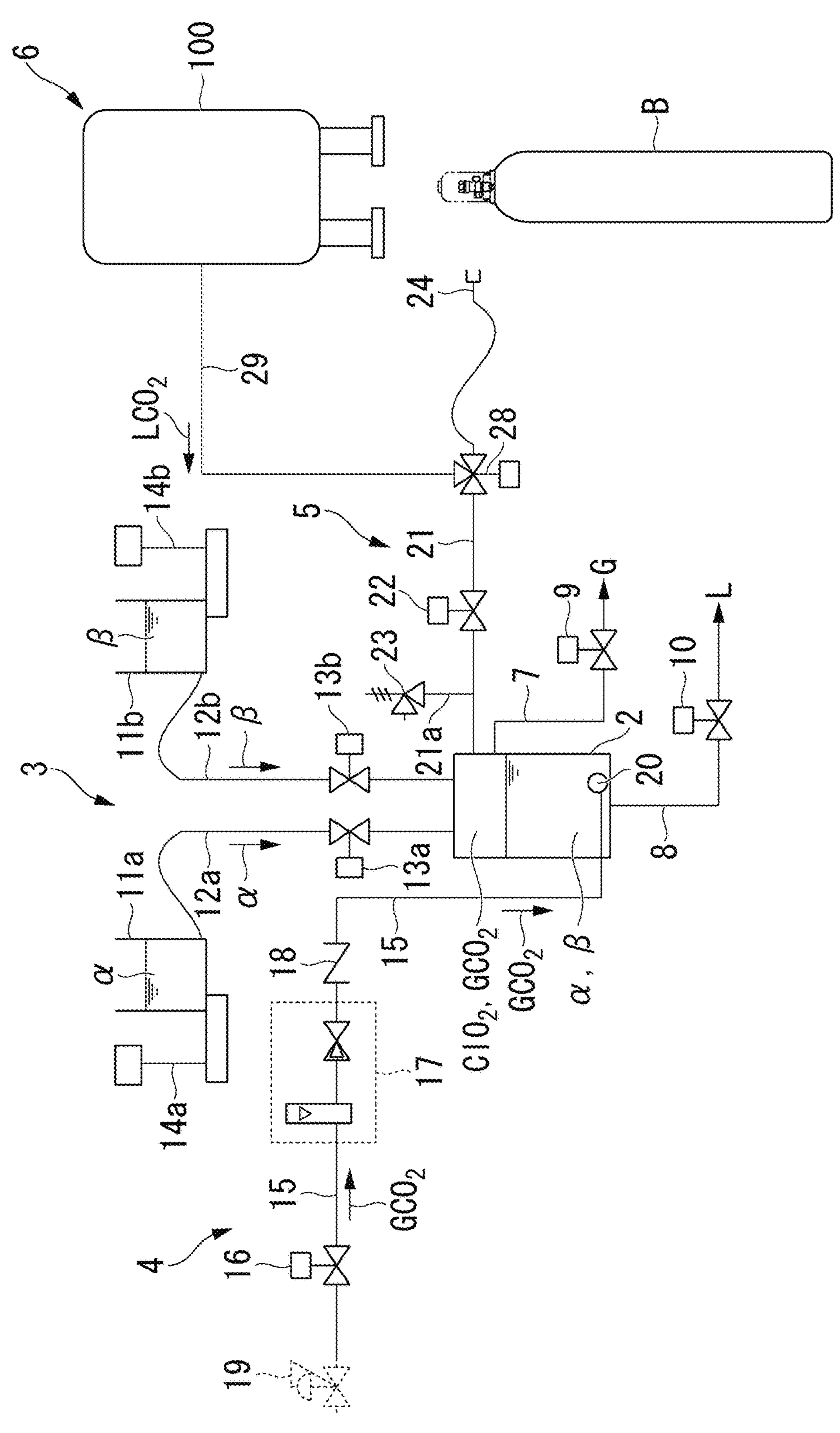
FIG. 3 is a schematic diagram showing a modified example of the system for producing a spray agent packed in a container shown in FIG. 1.

In addition, in the above-described production system 1, the above-described liquefied carbon dioxide gas charging unit 6 is configured independently, but for example, as shown in FIG. 3, it is also possible to configure the pressure-resistant container B to be charged with the liquefied carbon dioxide gas ($LCO_2$) supplied from a liquefied carbon dioxide gas supply pipe 29 connected to the chlorine dioxide discharge pipe 21 via a three-way valve 28.

Figure 4:
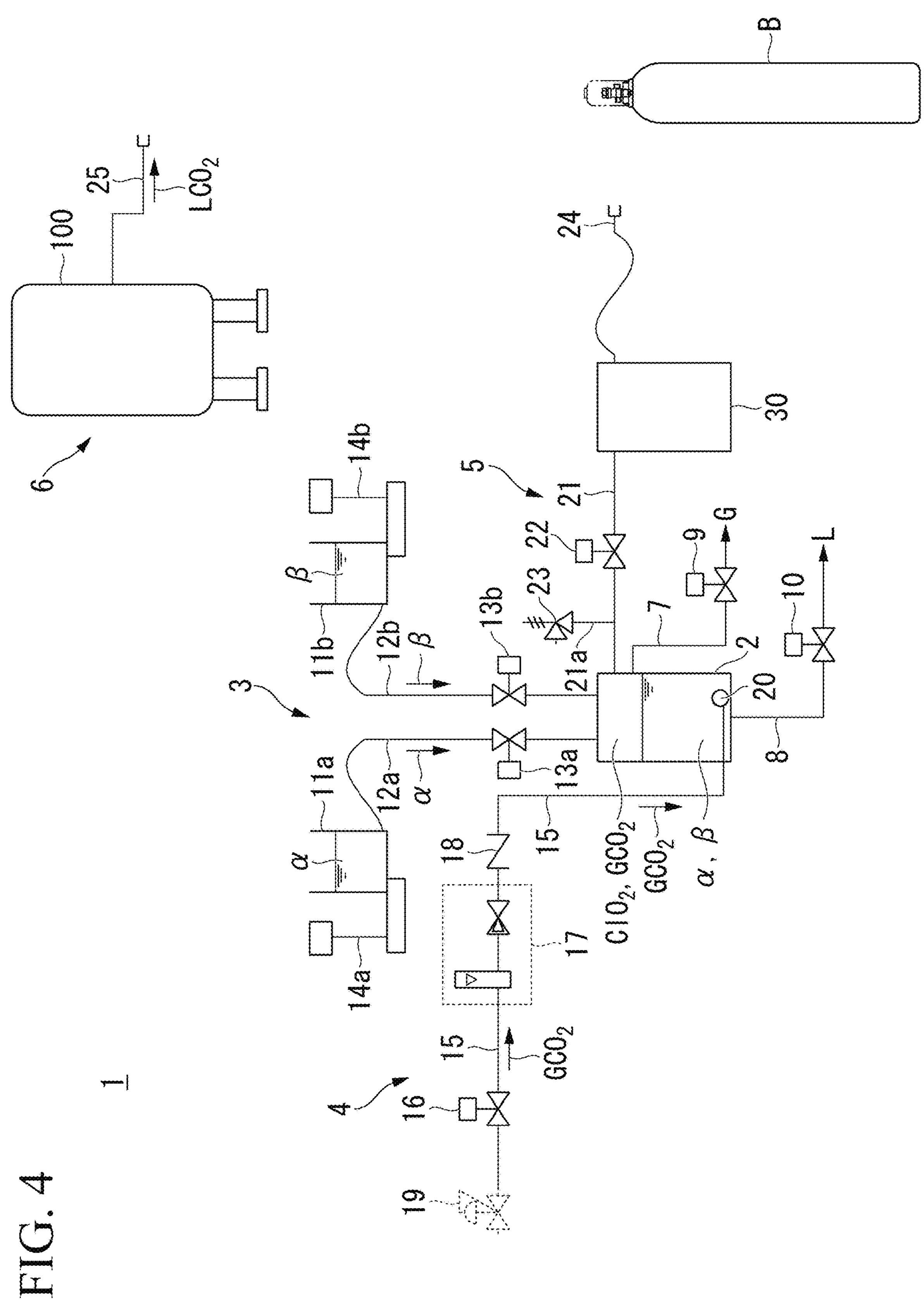
FIG. 4 is a schematic diagram showing a modified example of the system for producing a spray agent packed in a container shown in FIG. 1.

In addition, in the above-described production system 1, the chlorine dioxide ($ClO_2$) generated in the above-described reaction tank 2 is directly charged into the pressure-resistant container B together with the carrier gas ($GCO_2$), but for example, as shown in FIG. 4, the chlorine dioxide ($ClO_2$) may be temporarily stored in a storage tank 30 or the like and then charged into the pressure-resistant container B.

In addition, the spray agent packed in a container to which the present invention is applied contains chlorine dioxide ($ClO_2$) and liquefied carbon dioxide gas ($LCO_2$) charged into the above-described pressure-resistant container, and the chlorine dioxide is dissolved in the liquefied carbon dioxide gas within the pressure-resistant container, but alternatively, instead of the liquefied carbon dioxide gas ($LCO_2$), the same gas as the carrier gas, for example, nitrogen ($N_2$) gas, an inert gas such as argon (Ar) or helium (He), or dry air (synthetic air) may be charged as the spray gas.

REFERENCE SIGNS LIST

1 Production system of spray agent packed in container
2 Reaction tank
3 Chemical liquid supply unit
4 Carrier gas supply unit
5 Chlorine dioxide charging unit
6 Liquefied carbon dioxide gas charging unit
7 Waste gas pipe
8 Waste liquid pipe
9 First on-off valve
10 Second on-off valve
11*a* First chemical liquid tank
11*b* Second chemical liquid tank
12*a* First chemical liquid supply pipe
12*b* Second chemical liquid supply pipe
13*a* Third on-off valve
13*b* Fourth on-off valve
14*a*, 14*b* Load cell
15 Carrier gas supply pipe
16 Fifth on-off valve
17 Mass flow controller (MFC)
18 Check valve
19 Pressure reducing valve
20 Bubbler
21 Chlorine dioxide discharge pipe
22 Sixth on-off valve
23 Pressure relief valve
24 Connection hose
25 Connection hose
26 Buffer tank
27 Pressure sensor
28 Three-way valve
29 Liquefied carbon dioxide gas supply pipe
30 Storage tank
100 Tank or cylinder
α, β Chemical liquid
G Waste gas
L Waste liquid
$ClO_2$ Chlorine dioxide
$GCO_2$ Carbon dioxide gas (carrier gas)
$LCO_2$ Liquefied carbon dioxide gas
B Pressure-resistant container

The invention claimed is:

1. A method for producing a spray agent packed in a pressure-resistant container, comprising:
- generating chlorine dioxide;
- charging the pressure-resistant container with the chlorine dioxide; and
- dissolving the chlorine dioxide in liquefied carbon dioxide gas while the pressure-resistant container charged with the chlorine dioxide is charged with the liquefied carbon dioxide gas,
- wherein while the chlorine dioxide is generated by reacting a plurality of chemical liquids in a reaction tank, a carrier gas is flowed into the chemical liquids in the reaction tank to perform bubbling, and the chlorine dioxide generated in the reaction tank is charged into the pressure-resistant container together with the carrier gas.

2. The method for producing a spray agent packed in a pressure-resistant container according to claim 1, wherein carbon dioxide gas is used as the carrier gas.

* * * * *